(12) United States Patent
Arrington et al.

(10) Patent No.: US 6,185,999 B1
(45) Date of Patent: Feb. 13, 2001

(54) MINI-TENSION TESTER

(75) Inventors: Edward Lee Arrington, Owego; Richard Ronald Hall, Endwell, both of NY (US); Charles J. Maira, Duryea, PA (US)

(73) Assignee: International Business Machines Corporation, Armonk, NY (US)

( * ) Notice: Under 35 U.S.C. 154(b), the term of this patent shall be extended for 0 days.

(21) Appl. No.: 09/211,975

(22) Filed: Dec. 15, 1998

(51) Int. Cl.[7] .................................................. G01N 3/24
(52) U.S. Cl. ........................................................ 73/150 A
(58) Field of Search ........................... 73/150 A, 150 R, 73/827, 842, 849, 850

(56) References Cited

U.S. PATENT DOCUMENTS

| | | |
|---|---|---|
| 2,473,517 | 6/1949 | Freedman . |
| 3,019,644 | 2/1962 | Mancini . |
| 3,580,065 | 5/1971 | Strittmater et al. . |
| 3,789,660 | 2/1974 | Rubio et al. . |
| 4,577,912 | * 3/1986 | Snyder .................................. 384/2 |
| 5,279,166 | * 1/1994 | Ward et al. ........................... 73/794 |
| 5,404,751 | * 4/1995 | Beran et al. ...................... 73/150 A |
| 5,679,203 | 10/1997 | Sakai . |
| 5,686,670 | 11/1997 | Vanderlip . |

FOREIGN PATENT DOCUMENTS

| | | |
|---|---|---|
| 2-195231 | 8/1990 | (JP) . |
| 572665 | 9/1977 | (SU) . |

* cited by examiner

*Primary Examiner*—Max Noori
(74) *Attorney, Agent, or Firm*—Schmeiser, Olsen & Watts; Lawrence R. Fraley

(57) ABSTRACT

A compact tension testing apparatus for determining the peel strength of a circuit line or film bonded to a substrate. A force gauge is mounted on an apparatus using low friction air bearings to allow the force gauge to self-align with the peeling location of the circuit line or film, thereby providing essentially orthogonal positioning relative to the substrate.

11 Claims, 3 Drawing Sheets

MINI-TENSION TESTER

FIELD OF THE INVENTION

The present invention is in the field of tensile testing machines. More particularly, the present invention provides an improved apparatus and method for measuring the peel strength of a circuit line or film bonded to a substrate such as a circuit board. Also, the present invention relates to universal testing machines providing tensile, compressive, shear, bending, and torsion tests on a material sample.

BACKGROUND OF THE INVENTION

Tensile testing machines are commonplace. Typically, a material test sample is clamped to a horizontal platform, and a clamping device attached to a force gauge is lowered in a vertical direction and attached to the test sample. Means are provided to move the clamping device and force gauge in an upward direction, thereby causing a tensile force to be applied to the test sample.

Commonly, samples are destructively tested in a large tensile testing machine, wherein a sample to be tested must be sacrificially extracted from a larger specimen for the sake of the test. Once the test has been completed, the sample is usually discarded, which can be prove to be very costly.

Typical tensile testing machines used for laminate bond testing only provide peeling movement in one direction, so that the electrical circuit line or other sample on a substrate being tested must be lined up along the one direction of movement. Unfortunately, this requires the substrate to be repositioned and clamped whenever a circuit line has a directional orientation different from the previous test direction. Further, when peeling a circuit line from a substrate, the force gauge must be constantly moved in order to keep the force gauge directly over the peeling location. This is necessary in order to ensure that a true force reading of the force perpendicular to the substrate is being measured.

SUMMARY OF THE INVENTION

The present invention avoids the disadvantages of the prior art by providing a compact mini-tension tester. The mini-tension tester includes a base plate, a x-axis slide apparatus, a y-axis slide apparatus, a z-axis slide apparatus, a servo actuator assembly, a force gauge, a cable, and a gripper clamp.

A substrate with a film or circuit line bonded to its surface can be attached to the base plate using clamps, vacuum means, or other attaching systems. The z-axis slide apparatus is slidably attached to the y-axis slide apparatus and the y-axis slide apparatus is slidable attached to the x-axis slide apparatus. Air bearings, or other frictionless type mechanisms, are used to provide essentially friction free motion. Therefore, the z-axis slide apparatus can move essentially friction free to any location within the x and y plane.

A servo actuator assembly is attached to the z-axis slide apparatus, and a force gauge is attached to the servo actuator assembly. The force gauge preferably comprises a strain gauge load cell, although other types of force measurement devices may be used. A cable connects the force gauge to a gripper clamp that is attached to a test sample located on a substrate. The test sample may include, for example, a circuit line or film formed on a substrate such as a printed circuit board.

In order to measure the pull force required to pull a circuit line or film from a substrate, the substrate is firmly attached to the platform using a vacuum system. In order to obtain test data without destroying the substrate or affecting the operation of the circuitry on the substrate, sample test circuit lines are applied to the substrate during the production process. Preferably, the sample test circuit lines are only used to monitor the production process, and are not involved with any part of the electronic functioning of circuitry on the substrate. Therefore, these circuit lines may be peeled off the substrate for testing, without sacrificing the operational circuitry on the substrate.

During testing, the end of a circuit line is peeled from the substrate and grasped by the gripper clamp. Next, a servo actuator assembly in the z-axis slide apparatus displaces the force gauge, cable, and gripper clamp upward in the z-direction at a constant velocity, thereby providing an upward force that peels the circuit line away from the substrate. The servo actuator assembly is force limited to provide a maximum of about 20 pounds of force. The desired force reading is the force applied in a direction perpendicular to the substrate. In the present invention, the friction free air bearings in the x-axis slide apparatus and y-axis slide apparatus allow the z-axis slide apparatus to "walk" with the circuit line release or peel point. This ensures that the force applied to the release point of the circuit line is always perpendicular to the substrate. Therefore, the force gauge is always measuring the desired force, that is, the force perpendicular to the substrate.

The use of the mini-tension tester is not restricted to only providing tensile testing, but can also provide compressive, shear and bending material testing, and strength testing. For instance, compressive testing can be conducted by providing a rigid member between the force gauge and the test object. Then the force cell is moved along the z-axis direction toward the test object, thereby creating a compressive force on the test object. For applying shear force, a test object can be clamped onto the base plate in a direction such that the desired shear force is in line with the z-axis of the mini-tension tester. In another embodiment, a shear force can be applied to the test object by attaching the servo actuator assembly in a direction perpendicular to the z-axis. For this case, a shear force can be applied to a test object in a direction parallel to the base plate. If a test object is attached to the base plate in a cantilevered manner, the servo actuator assembly can apply a force in the z-axis direction to the free end of the cantilever causing a bending moment in the test object.

The present invention additionally provides a mini-tension tester that is compact enough to fit inside an oven to provide elevated temperature testing. The mini-tension tester is portable and versatile since a variety of substrate sizes can be attached to the base plate. Also, the mini-tension tester is much less costly then the large tensile testing machines that it replaces.

Generally, the present invention provides an apparatus for measuring the peel strength of a material bonded to a substrate, comprising:

a gripper clamp for grasping a material bonded to a surface of a substrate;

a force gauge attached to a z-axis displacement system and coupled to the gripper clamp, wherein a displacement of the z-axis displacement system causes the material to peel away from the substrate; and x and y-axis displacement systems attached to the z-axis displacement system for providing self-aligning orthogonal positioning of the force gauge relative to a release point of the material as the material is peeled away from the substrate.

BRIEF DESCRIPTION OF THE DRAWINGS

The features of the present invention will best be understood from a detailed description of the invention and a preferred embodiment thereof selected for the purposes of illustration and shown in the accompanying drawings in which.

DETAILED DESCRIPTION OF THE INVENTION

Figure 1:
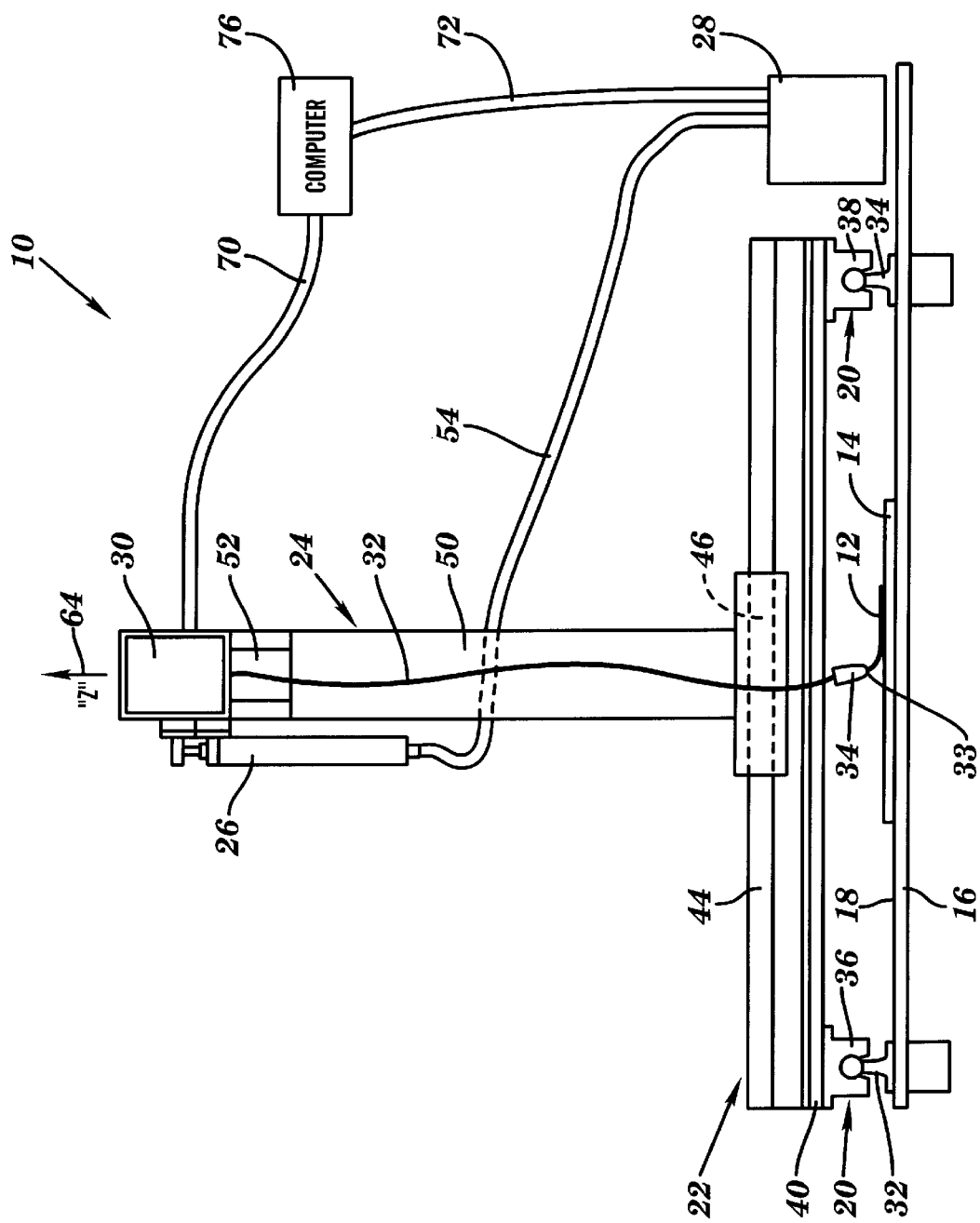
FIG. 1 illustrates a mini-tension tester according to a preferred embodiment of the present invention.

The features and advantages of the present invention are illustrated in detail in the accompanying drawings, wherein like reference numerals refer to like elements throughout the drawings.

Figure 2:
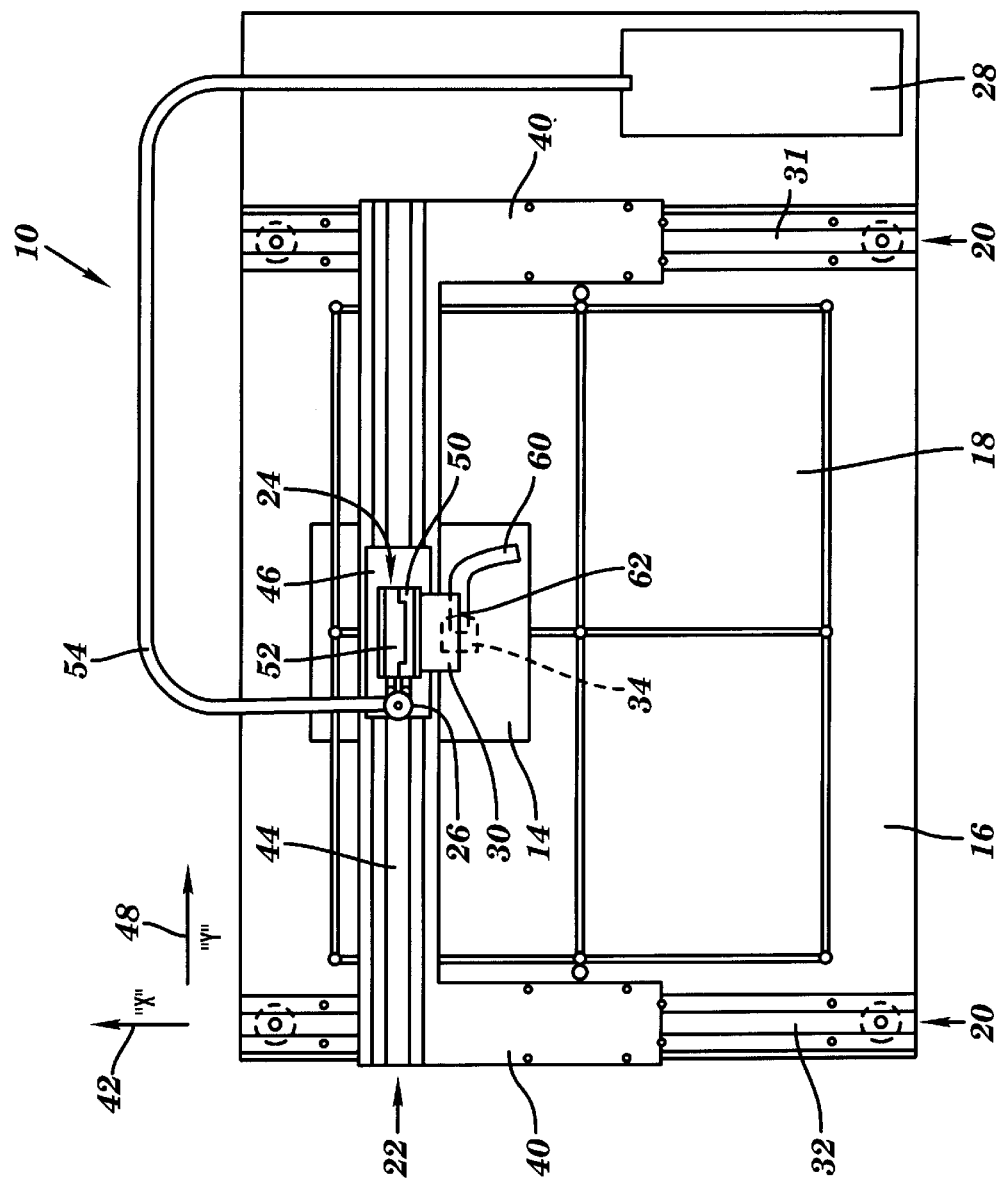
FIG. 2 illustrates a top perspective view of the mini-tension tester of FIG. 1.

A mini-tension tester 10 for measuring the peel strength of a film 12 bonded to a substrate 14 in accordance with a preferred embodiment of the present invention is illustrated in detail in FIGS. 1 and 2. The mini-tension tester 10 generally includes a base plate 16, a vacuum surface 18, an x-axis slide apparatus 20, a y-axis slide apparatus 22, a z-axis slide apparatus 24, a servo actuator assembly 26, a servo actuator controller 28, a force gauge 30, a cable 32, and a gripper clamp 34.

The x-axis slide apparatus 20 includes air bearing slides 32 and 31, air bearings 36 and 38, and bridge 40. Air bearings 36 and 38 are attached to the bridge 40 and slide essentially "friction free" on top of the air bearing slides 32 and 31. Therefore, the x-axis slide apparatus 20 allows essentially "friction free" motion of the bridge 40, in the "x" direction 42 as shown in FIG. 2.

The y-axis slide apparatus 22 includes an air bearing slide 44 and an air bearing 46. The air bearing 46 slides essentially "friction free" on top of the air bearing slide 44 in the "y" direction 48 as shown in FIG. 2.

The z-axis slide apparatus 24 includes a vertical post 50, a slide 52, and the air bearing 46. Air bearing 46 is rigidly attached to the vertical post 50. Slide 52 is slidingly attached to the vertical post 50. The force gauge 30 is attached to the slide 52. Servo actuator assembly 26 provides controlled relative motion between the slide 52 and the vertical post 50. Cable 32 connects the force gauge 30 to the gripper clamp 34 (FIG. 1).

The servo actuator controller 28 provides control signals to the servo actuator assembly 26 through control cable 54 to control the displacement of the slide 52 and attached force gauge 30 relative to the substrate 14. Preferably, a constant velocity motion is generated between the substrate 14 and the force gauge 30. However, a variable velocity motion may be used, depending on the type of testing being performed by the tester 10. As shown in FIG. 1, for example, with the gripper clamp 34 grasping the end 33 of the film 12 on the substrate 14, a constant velocity motion provided by the servo actuator assembly 26 results in the film 12 being peeled from the substrate 14 at a constant velocity. As the film 12 is being peeled from the substrate 14, the output from the force gauge 30 provides a continuous measurement of the force being applied to the film 12. Advantageously, the x-axis slide apparatus 20 and y-axis slide apparatus 22 are configured to continuously position, i.e., self-align, the force gauge 30 directly above the release point of the film 12 on the substrate such that the force gauge 30 is always measuring a force perpendicular to the substrate.

Referring again to FIG. 1, a computer or other type of processing system 76 can be used to gather force measurement data through cable 70 and positional data through cable 72. Cable 70 connects the force gauge 30 to the computer 76, and cable 72 connects the servo actuator controller 28 to the computer 76. The servo actuator controller 28 provides information regarding the position and movement of the servo actuator assembly 26. Therefore, the computer 76 can be used to gather the force measurement, along with time and displacement measurements, as a test is being conducted.

FIG. 2 illustrates the peel strength testing of a circuit line 60 on a substrate 14. The circuit line 60 may be a sample test line or may comprise a portion of the operational circuitry on the substrate 14. Initially, a first end 62 of the circuit line 60 is peeled off of the substrate 14 and gripped by the gripper clamp 34. Next, the servo actuator assembly 26 in the z-axis slide apparatus 24 displaces the slide 52, force gauge 30, cable 32 and gripper clamp 34 at a constant velocity in an upward "z" direction 64 (see FIG. 1). This upward motion provides an upward force that peels the circuit line 60 away from the substrate 14 (FIG. 2). Since the force gauge 30 is positioned above the release point of the circuit line 60, the force measured by the force gauge 30 is the force applied to the circuit line 60 in the "z" direction 64 that is perpendicular to the substrate 14.

As the slide 52, force gauge 30, cable 32 and gripper clamp 34 continue to be displaced at a constant velocity in an upward "z" direction, the z-axis slide apparatus 24 "walks" with the circuit line 60 release point, even if the circuit line 60 changes direction (FIG. 2). That is, the force required to peel the circuit line 60 away from the substrate 14 additionally causes the z-axis slide apparatus 24 to be pulled along with, and continuously positioned above, the release point of the circuit line 60. Such self-aligning displacement of the z-axis slide apparatus 24 is provided through the use of the air bearing structure of the x-axis slide apparatus 20 and the y-axis slide apparatus 22. Therefore, essentially "friction free" motion of the z-axis slide apparatus 24 is provided in the "x-y" plane. Thus, in the preferred embodiment of the present invention, the force gauge 30 is always measuring the force that is perpendicular to the substrate 14.

Figure 3:
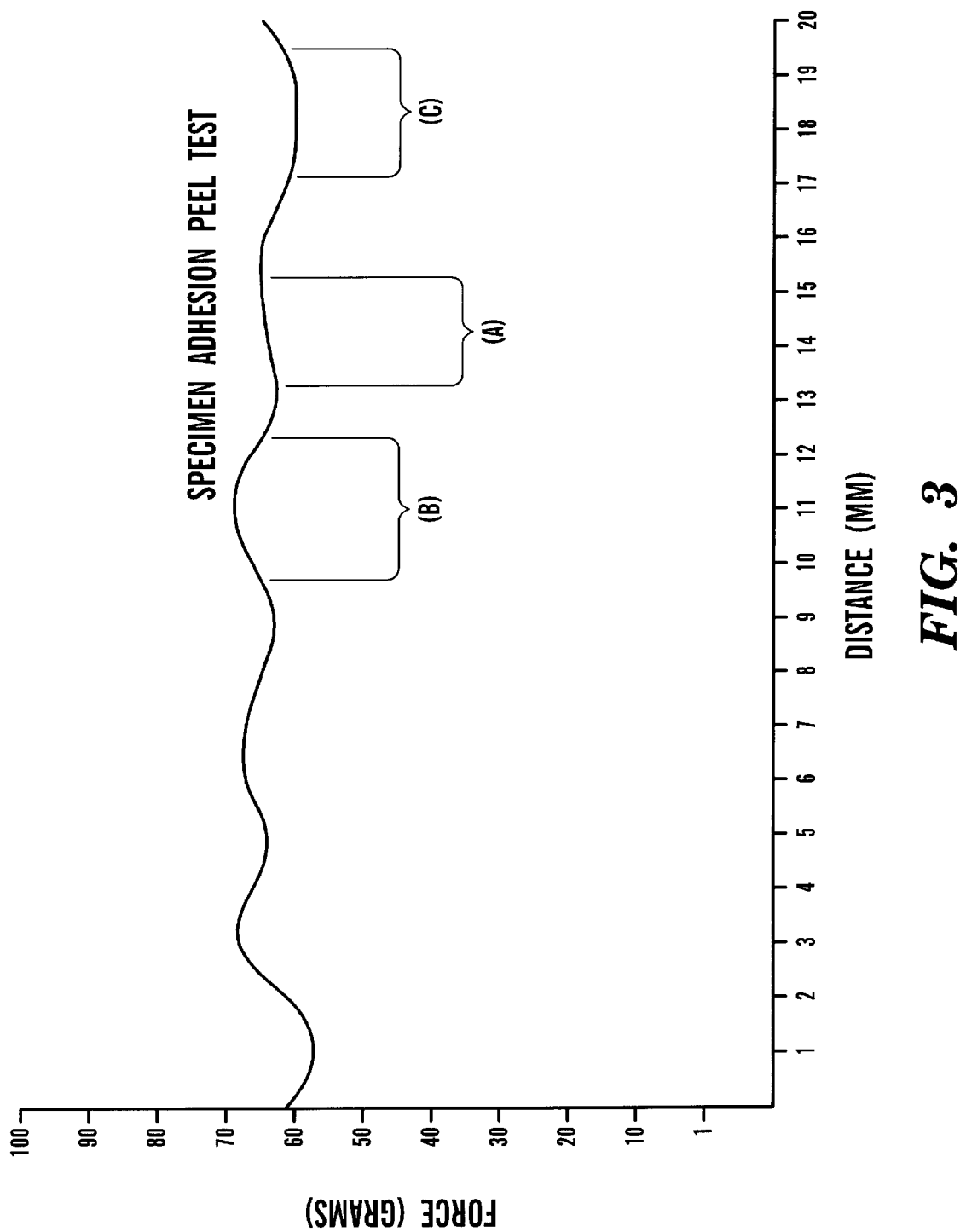
FIG. 3 illustrates a graph of force versus peel distance along a circuit line.

Referring to FIG. 3, a graph of the force measured by the force gauge 30 versus the peel distance along the substrate 14 can be used for evaluation of the bonding strength along the circuit line 60. If the bonding strength is uniform along the circuit line 60, the graph of force versus peel distance will form an essentially horizontal line as illustrated in region (A) on FIG. 3. If the bonding strength is higher in one region along the circuit line 60, then the graph of force versus peel distance will form an upward spike, as illustrated in region (B) on FIG. 3. If the bonding strength is lower in one region along the circuit line 60, then the graph of force versus peel distance will form a downward spike, as illustrated in region (C) on FIG. 3. Therefore, the graph of force versus peel distance provides information on the quality of the bonding strength along the circuit line 60.

The cable 32 preferably has a predetermined minimum length to limit the effect of a temporary deflection of the cable 32 on the force value measured by the force gauge 30. Such a temporary deflection may occur, for example, if a large section of the circuit line 60 suddenly releases from the substrate 14 during testing. The minimum length of the cable 32 is chosen to minimize the deviation of the force application angle on the force gauge 30. In the preferred embodiment of the present invention, a minimum cable length of about 18 inches has proven to be adequate.

The foregoing description of the present invention has been presented for purposes of illustration and description. It is not intended to be exhaustive or to limit the invention to the precise form disclosed, and many modifications and variations are possible in light of the above teaching. Such modifications and variations that may be apparent to a person skilled in the art are intended to be included within the scope of this invention as defined by the accompanying claims.

We claim:

1. An apparatus for measuring the peel strength of a material bonded to a substrate, comprising:
    a gripper clamp for grasping a material bonded to a surface of a substrate positioned in an x-y plane;
    a force gauge attached to a z-axis displacement system and coupled to the gripper clamp, wherein a displacement of the z-axis displacement system causes the material to peel away from the substrate, wherein the z-axis displacement system comprises a movable member for supporting the force gauge, and a system for displacing the movable member along the z-axis; and
    x and y-axis displacement systems attached to the z-axis displacement system for providing self-aligning orthogonal positioning of the force gauge relative to a release point of the material as the material is peeled away from the substrate;
wherein the x-axis displacement system comprises a plurality of air bearing slides, a bridge, and a plurality of air bearings for supporting the bridge on the plurality of air bearing slides.

2. The apparatus according to claim 1, wherein the y-axis displacement system comprises:
    an air bearing slide mounted to the bridge; and
    an air bearing attached to the movable member of the z-axis displacement system and coupled to the air bearing slide mounted to the bridge.

3. An apparatus for measuring the peel strength of a material bonded to a substrate, comprising:
    a gripper clamp for grasping a material bonded to a surface of a substrate;
    a force gauge attached to a first displacement system and coupled to the gripper clamp, wherein a displacement of the first displacement system relative to the substrate causes the material to peel away from the substrate; and
    second and third displacement systems attached to the first displacement system for providing self-aligning orthogonal positioning of the force gauge relative to a release point of the material as the material is peeled away from the substrate.

4. The apparatus according to claim 3, wherein the material is a circuit line.

5. The apparatus according to claim 3, wherein the material is a film.

6. The apparatus according to claim 3, wherein the substrate is a circuit board.

7. The apparatus according to claim 3, wherein the first and second displacement systems are configured to provide substantially frictionless displacement of the first displacement system relative to the substrate.

8. The apparatus according to claim 3, wherein the first displacement system comprises:
    a movable member for supporting the force gauge; and
    a system for displacing the movable member along a first axis.

9. The apparatus according to claim 8, wherein the second displacement system comprises:
    a plurality of air bearing slides;
    a bridge; and
    a plurality of air bearings for supporting the bridge on the plurality of air bearing slides to provide displacement of the bridge along a second axis.

10. The apparatus according to claim 9, wherein the third displacement system comprises:
    an air bearing slide mounted to the bridge; and
    an air bearing attached to the movable member of the first displacement system and coupled to the air bearing slide mounted to the bridge to provide displacement of the first displacement system along a third axis.

11. The apparatus according to claim 10, wherein the first, second and third axes are orthogonal to one another.

* * * * *